(12) United States Patent
Perin

(10) Patent No.: US 7,237,445 B1
(45) Date of Patent: Jul. 3, 2007

(54) TEST FIXTURE FOR THE AGING OF WIPER BLADES IN A LABORATORY

(75) Inventor: Giovanni Perin, Rochester Hills, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 122 days.

(21) Appl. No.: 11/236,134

(22) Filed: Sep. 27, 2005

Related U.S. Application Data

(60) Provisional application No. 60/638,050, filed on Dec. 21, 2004.

(51) Int. Cl.
*G01M 19/00* (2006.01)
*G01N 3/56* (2006.01)
*A47L 1/02* (2006.01)

(52) U.S. Cl. ................ 73/865.3; 73/7; 73/9; 73/865.8

(58) Field of Classification Search .............. 73/7, 73/8, 9, 662, 663, 670, 671, 841, 855, 856, 73/858, 860, 866, 865.3, 865.8; 248/157, 248/161; 15/247

See application file for complete search history.

(56) References Cited

U.S. PATENT DOCUMENTS

| | | | | |
|---|---|---|---|---|
| 2,472,006 A | * | 5/1949 | Dosker | 144/263 |
| 2,487,944 A | * | 11/1949 | Pressman | 33/561.3 |
| 4,103,385 A | * | 8/1978 | Porter | 15/250.48 |
| 4,579,271 A | * | 4/1986 | Fujita et al. | 228/46 |
| 4,800,054 A | * | 1/1989 | Roestenberg | 264/86 |
| 4,910,088 A | * | 3/1990 | Baudin et al. | 428/432 |
| 4,912,803 A | * | 4/1990 | Yasukawa et al. | 15/250.48 |
| 5,114,454 A | * | 5/1992 | Promper et al. | 65/163 |
| 5,225,752 A | * | 7/1993 | Yasuda et al. | 318/443 |
| 5,472,168 A | * | 12/1995 | Tapp | 249/139 |
| 6,025,025 A | * | 2/2000 | Bartrug et al. | 427/302 |
| 6,057,660 A | * | 5/2000 | Meier et al. | 318/483 |
| 6,077,592 A | * | 6/2000 | Azuma et al. | 428/192 |
| 7,028,367 B2 | * | 4/2006 | Sharabura et al. | 15/250.001 |
| 2003/0110827 A1 | * | 6/2003 | Kamitani et al. | 73/7 |

FOREIGN PATENT DOCUMENTS

| | | | | |
|---|---|---|---|---|
| DE | 2932461 A | * | 2/1981 | |
| EP | 589680 A2 | * | 3/1994 | |
| JP | 2001141610 A | * | 5/2001 | |
| KR | 2002017294 A | * | 3/2002 | |

* cited by examiner

*Primary Examiner*—Hezron Williams
*Assistant Examiner*—David A. Rogers
(74) *Attorney, Agent, or Firm*—Gigette M. Bejin; Miller Law Group, PLLC

(57) ABSTRACT

A test fixture facilitates the laboratory testing of windshield wiper blades for vehicles. The test fixture includes a base frame on which are mounted a number of windshield wiper arms oriented generally parallel for engagement with a stainless steel test surface. Positionally adjustable supports are mounted on the base frame to configure the test surface by varying the curvature of the test surface, as well as the overall length thereof, to permit simulation of a large variety of automotive windshields for test purposes. The test fixture also includes a wiper arm mounting device that can be manipulated to vary the wiper arm load to the wiper blade on the test surface. Adjustments in the spring force exerted on the wiper blade allow variances in the application of a biasing force on the wiper blade in conjunction with changes in the attack angle.

20 Claims, 7 Drawing Sheets

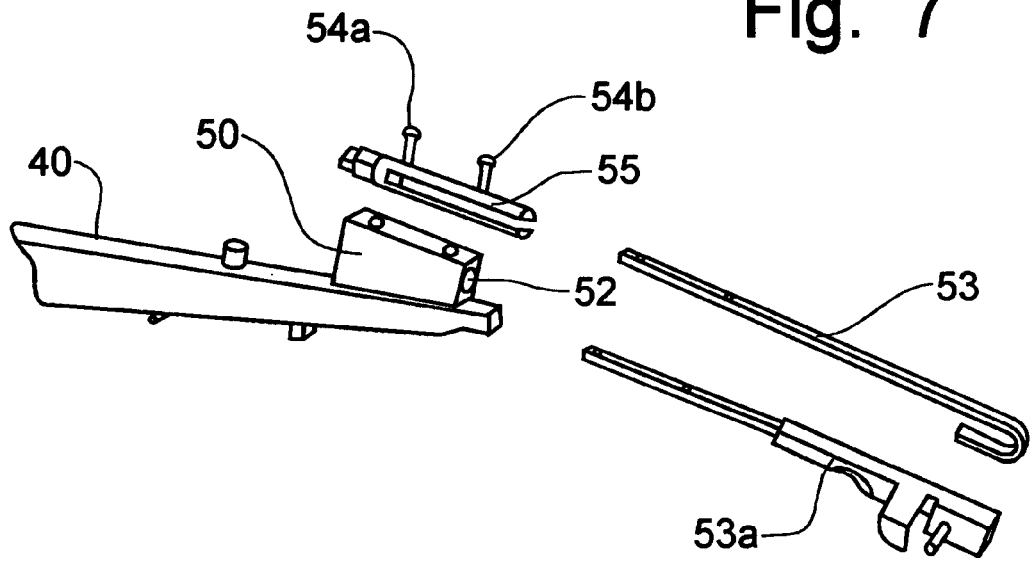
Fig. 7
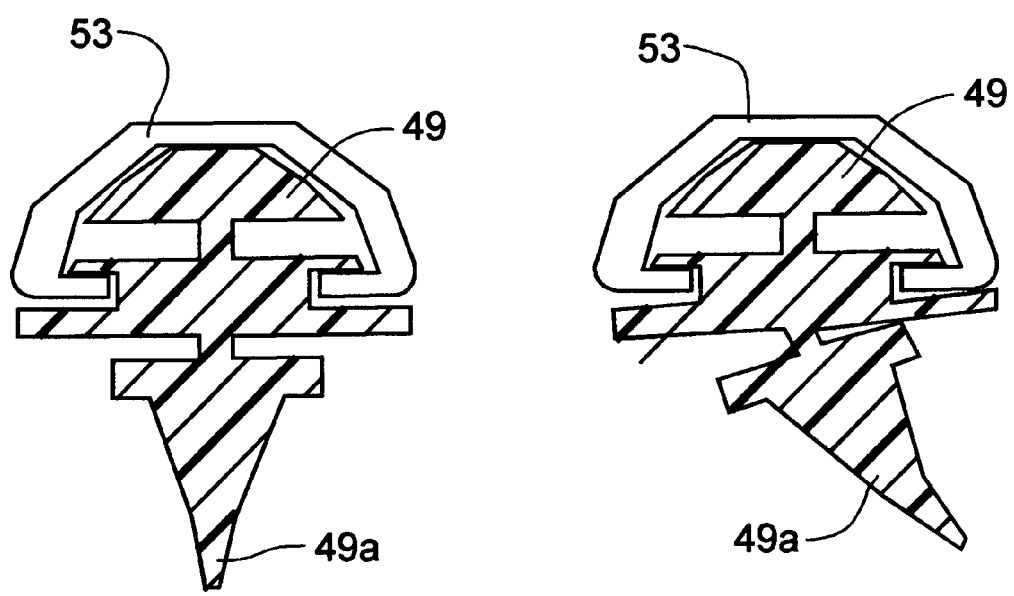
Fig. 8A
Fig. 8B

TEST FIXTURE FOR THE AGING OF WIPER BLADES IN A LABORATORY

CROSS-REFERENCE TO RELATED APPLICATIONS

This application claims domestic priority on U.S. Provisional Patent Application Ser. No. 60/638,050, filed on Dec. 21, 2004, the contents of which are incorporated herein by reference.

FIELD OF THE INVENTION

This invention relates to a device for testing wiper blades for automobiles and, more particularly, to a fixture for aging wiper blades to replicate the real world environment to which wiper blades are exposed.

BACKGROUND OF THE INVENTION

Wiper blades are a high use item on automobiles and require frequent replacing during the operative life of an automobile primarily due to the aging of the elastomeric material from which the wiper blade is manufactured. Aging of the wiper is a function of the exposure of the wiper blade to the environment and of the external forces exerted on the wiper blade from the mounting arms and the curvature of the windshield glass over which the wiper blade is operated.

To develop improved wiper blades and to enhance their overall performance, it is preferable to replicate the real world utilization of the wiper blades in the laboratory, particularly under lab conditions that can accelerate the aging process. Laboratory testing of wiper blades would require a process and a test fixture by which the wiper blades can be subjected to accelerated tests. Historically, such a process and test fixture has not been developed adequately.

In order to replicate and improve wiper blade performance, the test fixture must be capable of reproducing the permanent set, stress and aging that the wiper blade is subjected to over time. Furthermore, the structural environment in which the wiper blades are to operate can vary significantly from one type or model of vehicle to the other. Accordingly, the test fixture must have sufficient flexibility to vary the parameters under which wiper blades can be operated. For example, the curvature of the windshield glass varies substantially from vehicle to vehicle. The spring force or load vector urging the wiper blade against the surface of the windshield can also be a significant variable. The attack angle, which is the angle at which the wiper blade is disposed against the windshield, is also a variable.

Accordingly, it would be desirable to provide a test fixture that can replicate the real world environment for the testing of wiper blades in a laboratory in which the test fixture will have sufficient flexibility to vary the operative parameters under which the wiper blades can be operable from one vehicle to another and within the same vehicle.

SUMMARY OF THE INVENTION

It is an object of this invention to overcome the aforementioned disadvantages of the known prior art by providing a fixture for the laboratory testing of wiper blades.

It is another object of this invention to provide a test fixture that will incorporate sufficient flexibility to vary the physical environmental parameters under which wiper blades operate in the rear world.

It is a feature of this invention that the shape of the test surface over which the wiper blades are to be tested can be varied to reflect the different configurations of vehicle windshields.

It is an advantage of this invention that many different windshield configurations can be simulated with the test fixture.

It is another feature of this invention that the both the length and the curvature of the test surface can be varied as needed to simulate different vehicle windshields.

It is still another feature of this invention that the attack angle of the wiper blade on the test surface can be varied.

It is yet another feature of this invention that the spring force exerted by a windshield wiper arm can be selectively varied to change the conditions under which the wiper blades are tested.

It is still another advantage of this invention that multiple wiper blade test simulations can be conducted simultaneously to determine the optimum parameters under which different wiper blades should be operated.

It is still another feature of this invention that the test fixture accommodates the mounting of different types of wiper blade mounts to provide greater flexibility in the utilization of the laboratory test fixture.

It is yet another advantage of this invention that the two differently configured test surfaces can be arranged on each base frame to test driver and passenger windshield glass curvature.

It is a further advantage of this invention that the configuration of the test surface can be quickly converted between different configurations simply by positionally adjusting the supports for the test surface.

It is a further feature of this invention that the base frame can be equipped with support legs that allow a stacking of multiple test fixtures for simultaneous operation in a compact space.

It is a further object of this invention to provide a wiper blade test fixture which is durable in construction, inexpensive of manufacture, carefree of maintenance, facile in assemblage, and simple and effective in use.

These and other objects, features and advantages are accomplished according to the instant invention by providing a test fixture for the laboratory testing of windshield wiper blades for vehicles. The test fixture includes a base frame on which are mounted a number of windshield wiper arms oriented generally parallel for engagement with a stainless steel test surface. Positionally adjustable supports are mounted on the base frame to configure the test surface by varying the curvature of the test surface, as well as the overall length thereof, to permit simulation of a large variety of automotive windshields for test purposes. The test fixture also includes a wiper arm mounting device that can be manipulated to vary the wiper arm load to the wiper blade on the test surface. Adjustments in the spring force exerted on the wiper blade allow variances in the application of a biasing force on the wiper blade in conjunction with changes in the attack angle.

BRIEF DESCRIPTION OF THE DRAWINGS

The advantages of this invention will become apparent upon consideration of the following detailed disclosure of the invention, especially when taken in conjunction with the accompanying drawings wherein:

FIG. 7 is an exploded perspective view of the end of the mounting device shown in FIG. 6, but with the mounting rod being disassembled from the mounting block of the adjustment apparatus, an alternative embodiment of the mounting rod is shown adjacent the mounting rod depicted in FIG. 6;

FIG. 8A is a cross-sectional view of a representative wiper blade showing the configuration of the wiper blade as the blade is manufactured;

FIG. 8B is a cross-sectional view of the representative wiper blade shown in FIG. 8A after undergoing aging, the wiper portion of the blade being deflected into a permanent set relative to the structural body of the blade retained in the mounting apparatus.

DETAILED DESCRIPTION OF THE PREFERRED EMBODIMENT

Figure 9:
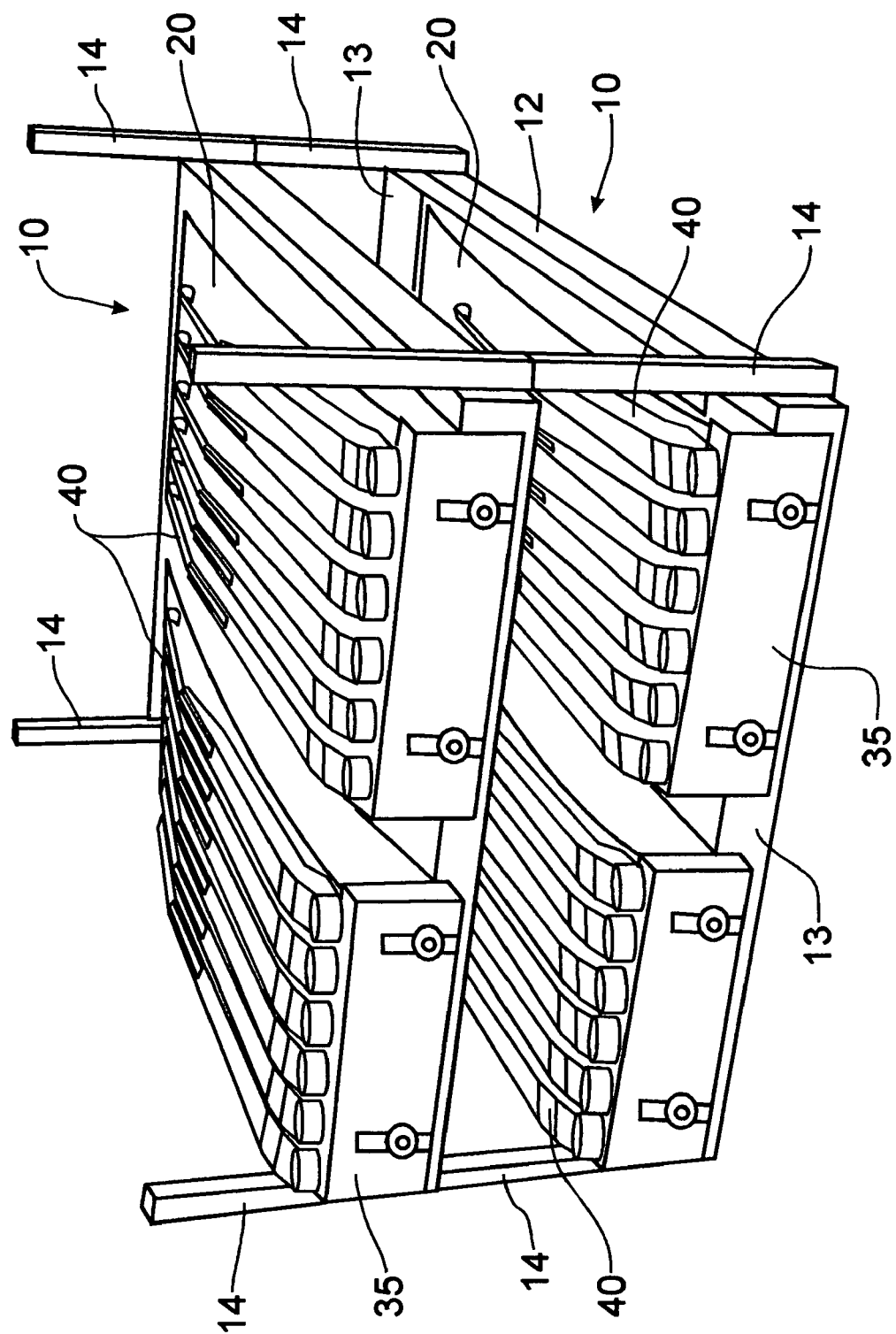
FIG. 9 is a schematic perspective view of a pair of stacked test fixtures permitted by the support legs on the frame structure to allow a large sample of wiper blades to be aged simultaneously.

Referring to FIGS. 1-4, a test fixture for testing wiper blades under laboratory conditions incorporates the principles of the instant invention. The test fixture 10 includes a frame 11 preferably manufactured from aluminum and formed from a pair of side beams 12 and a pair of end beams 13 with four upright support posts 14 positioned near the four corners of the rectangular frame 11. The upright support posts 14 are utilized, as is depicted in FIG. 9 to stack multiple test fixtures; therefore, the upright posts 14 have to be configured to be stackable such as by having the upper ends of the posts 14 sized to fit within the bottom ends of the posts 14.

Figure 1:
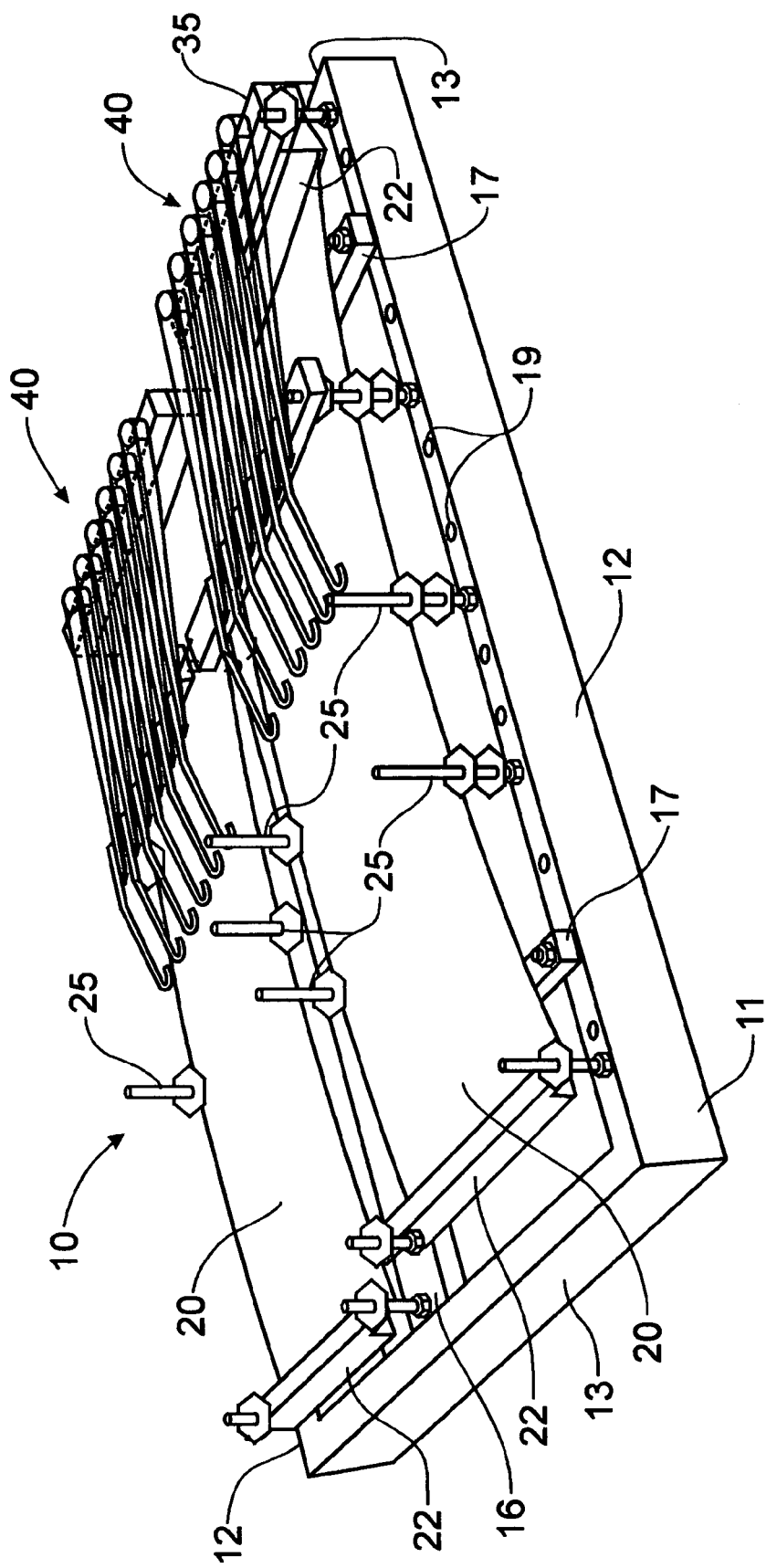
FIG. 1 is a schematic perspective view of a wiper blade test fixture incorporating the principles of the instant invention, the individual wiper blades being removed from the test fixture for purposes of clarity.
Figure 4:
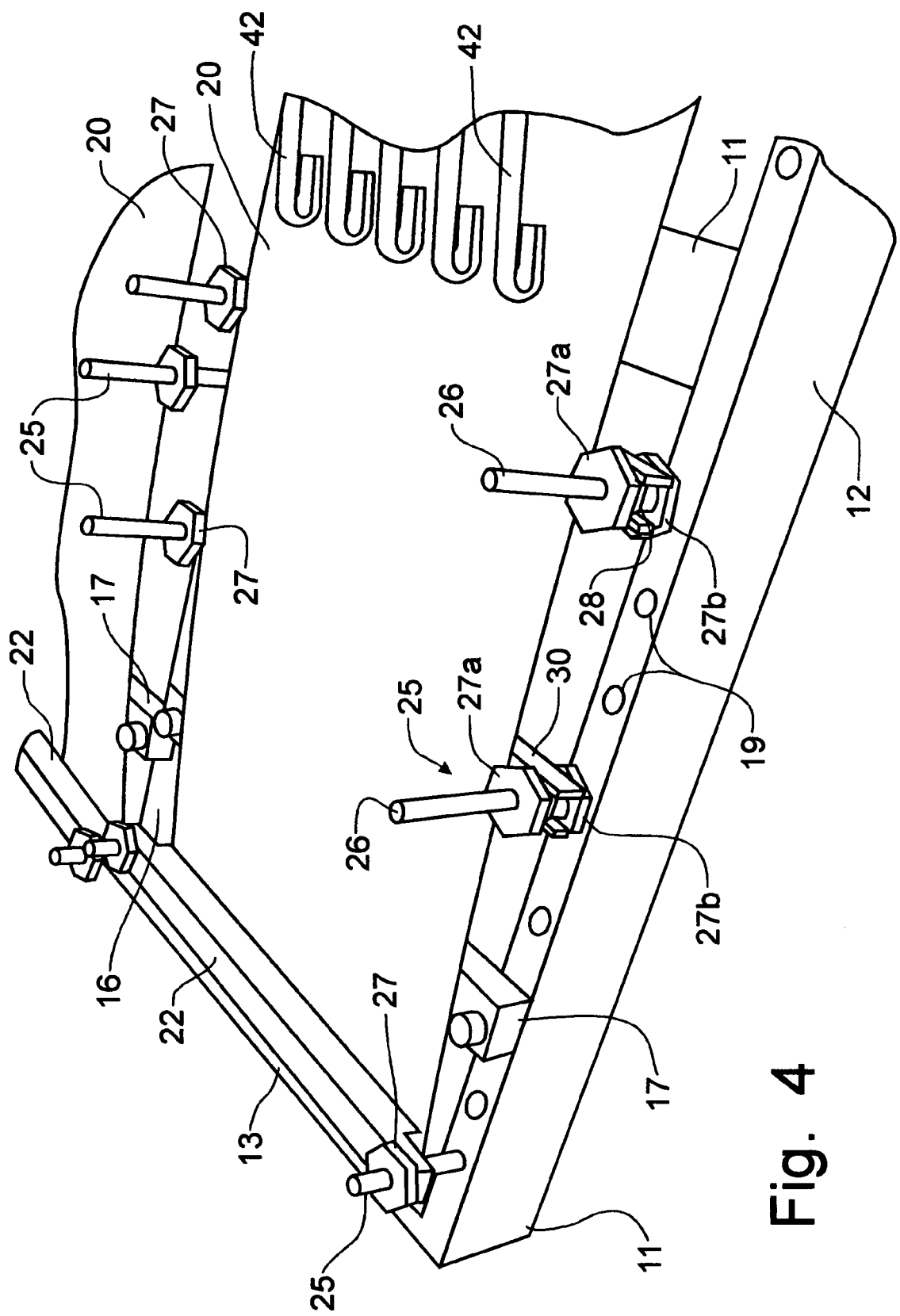
FIG. 4 is a partial upper perspective view of the end of the test fixture opposite the head portion to depict the support of the test surfaces over which the wiper blades are engaged, the individual wiper blades being removed from the fixture for purposes of clarity.

The rectangular frame 11 is formed with a center support beam 16 that is oriented parallel to the side beams 12 and located midway between the side beams 12 to provide support for the plates 20 that provide a test surface against which the wiper blades will be engaged, as will be described in greater detail below. The frame 11 is also formed with a pair of fixed support bars 17 spanning between the respective side beams 12 and the center support beam 16. The fixed support bars 17 are located, as is best seen in FIGS. 1 and 4, near the end beams 13, but spaced inwardly somewhat to provide support for the curvature of the plates 20 to be described in greater detail below.

Preferably, each test fixture 10 is provided with a pair of flexible plates 20, preferably formed of stainless steel with a mirror finish on the top surface thereof. One skilled in the art will readily recognize that the number of plates 20 provided on the test fixture 10 could be more or less than two, with appropriate structure changes to the frame 11 as would be required to support the plates 20 in the manner described below. The plates 20 are mounted at opposing ends by a push down bar 22 located near each opposing end beam 13. The push down bars 22 provide support for the ends of the plate 20 and provide vertical restraint on the respective ends of the plate 20 to permit the plates 20 to be curved as desired. The push down bars 22 have sufficient depth to accommodate the changes in the length of the plates 20 caused by varying the curvature of the plates 20.

The side beams 12 and the center support beam 16 of the frame 11 are formed with a plurality of threaded holes 19 along the length thereof between the respective fixed support bars 17, preferably eight to ten holes 19, though only a representative number of the holes 19 are depicted in the drawings, to provide adequate flexibility to form the plates 20 in the curvature desired. A plurality of support members 25 having threaded rods 26, best seen in FIGS. 1-4, are threaded into selected holes 19 along the length of the side beams 12 and center support beam 16. The support members 25 are arranged in pairs located on opposite transverse sides of the plate 20. An adjustable cross bar 30 extends between the corresponding pair of opposing support members 25 to support the flexible plate 20 between the support members 25. The quantity and location of support members 25 and the adjustable cross bars 30 is determined by the desired complexity of the curved formation of the respective flexible plate 20.

Figure 3:
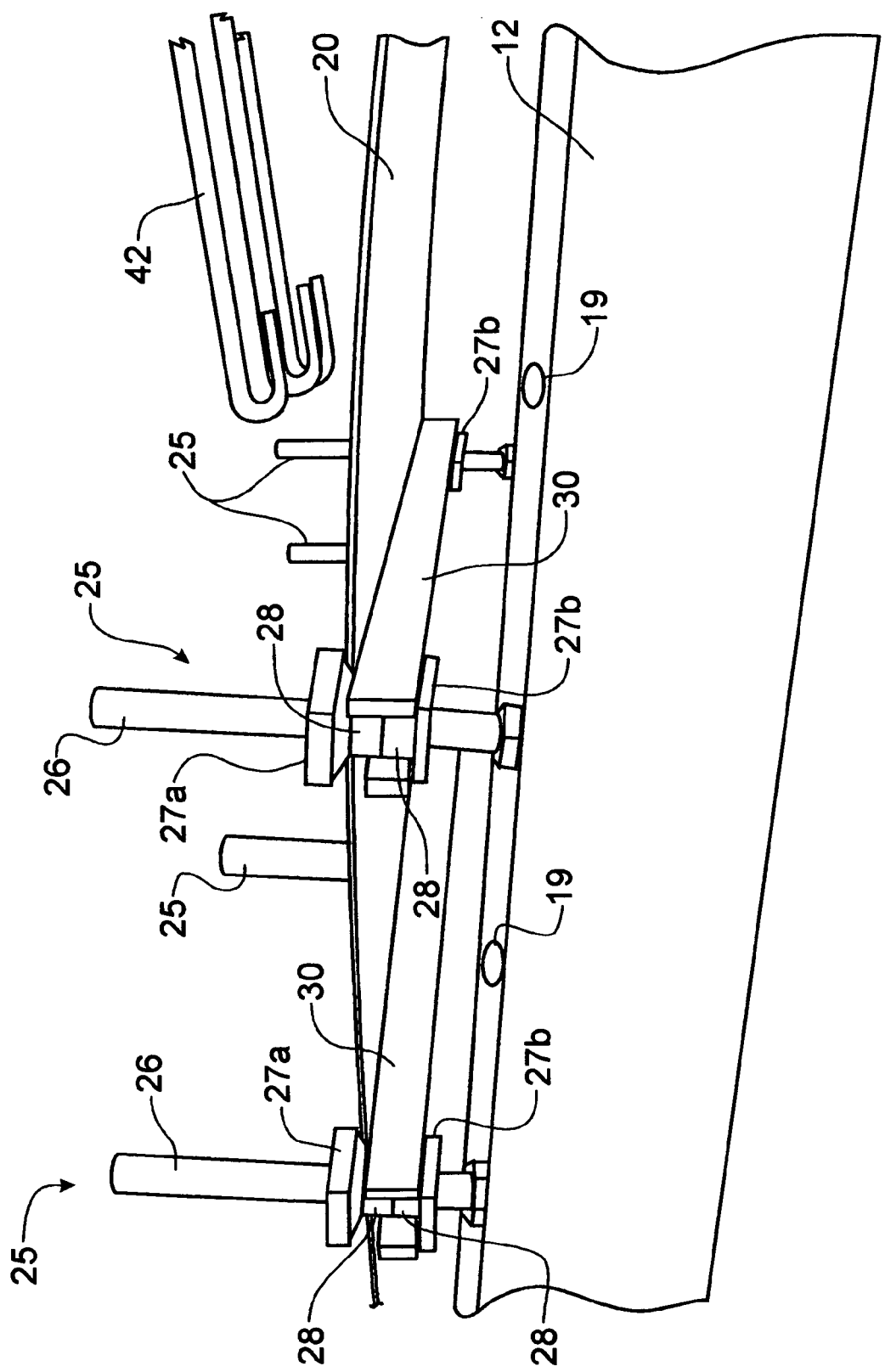
FIG. 3 is a partial side perspective view of the test fixture shown in FIG. 1 to show the support of the test surface for the adjustable configuration thereof to replicate differently shaped automotive windshields.

Each threaded rod 26 has mounted thereon a pair of bronze nuts 27 with each of the bronze nuts 27 having an enlarged head 28. The bronze nuts 27 are mounted on the threaded rod 26 in opposing fashion with the bottom bronze nut 27b having the head 28 at the bottom of the nut 27 and the top bronze nut 27a having the head 28 at the top of the nut 27, as is best seen in FIG. 3. The two bronze nuts 27 are preferably positioned next to each other so that the bottom bronze nut 27b will support the adjustable cross bar 30 on the head 28 thereof while the top bronze nut 27a secures the plate 20 against the adjustable cross bar 30.

One of ordinary skill in the art will recognize that the height of the bronze nuts 27 on each individual pair of threaded rods 26 is vertically adjustable by threading the nuts 27 along the length of the rod 26. By properly positioning the bronze nuts 27, and, therefore, the position of the adjustable cross bars 30, at each pair of support members 25, and providing an adequate number of pairs of support members 25, the precise curvature of the plate 20 can be finely adjusted and tuned to mimic substantially any automotive windshield surface. The plates 20 are trapped between the push down bars 22 at the ends of the plates 20, on top of the fixed support bars 17, and between the longitudinally spaced adjustable cross bars 30 with the upper bronze nuts 27a securing the plate 20 against the adjustable cross bars 30.

Figure 2:
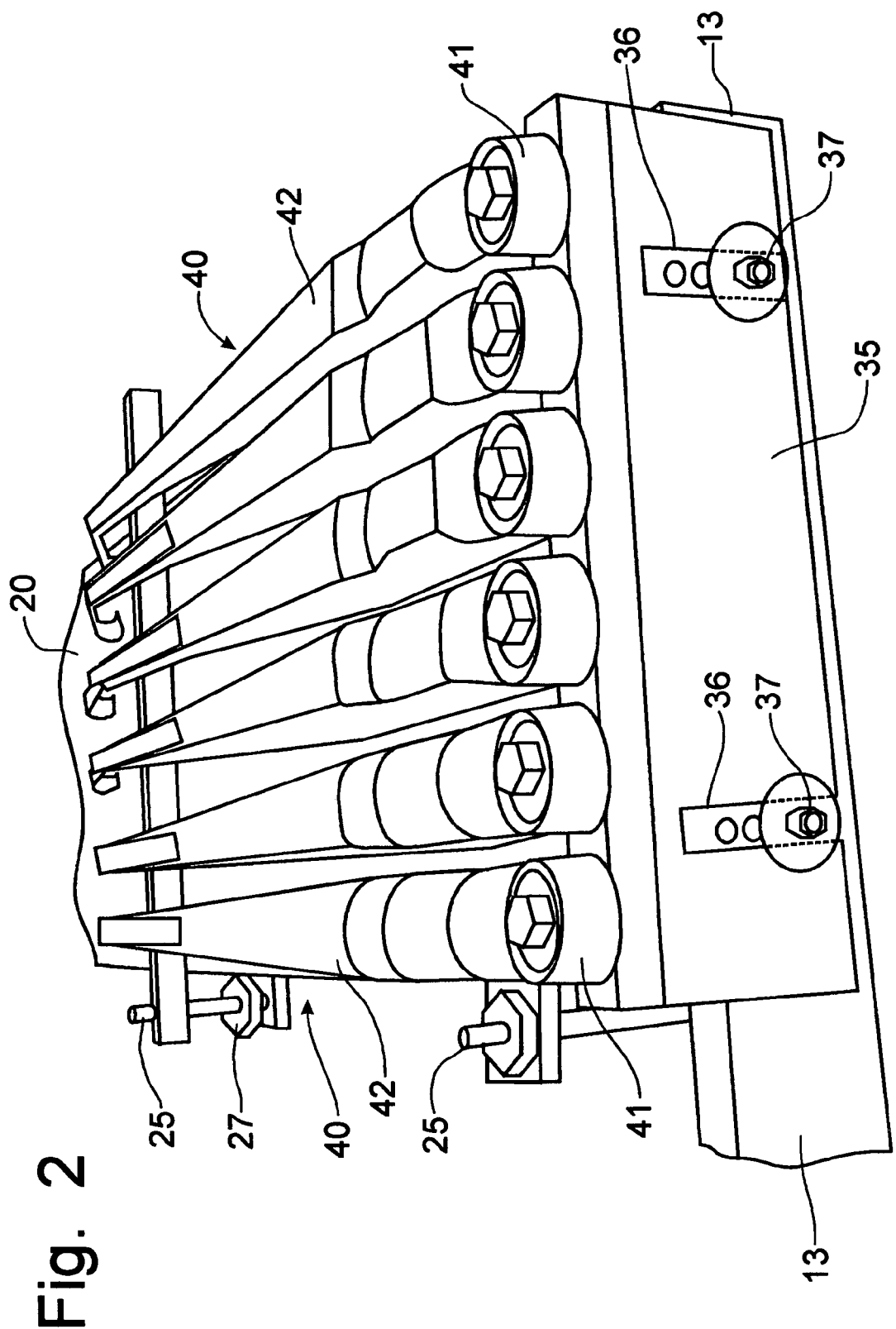
FIG. 2 is a partial perspective end view of the head portion of the test fixture shown in FIG. 1.

At the head portion 15 of the frame 11, as best seen in FIG. 2, the end beam 13 has a pair of blocks 35 bolted thereto to provide support for adjustable arms 40 that will support the wiper blades 49 against the plates 20. One of the blocks 35 correspond to each of the plates 20 and incorporate vertically slotted openings 36 for the passage of fasteners 37 connecting the blocks 35 to the end beam 13. The vertical slots 36 permit a vertical and angular positional adjustment of the block 35 relative to the end beam 13 on which the block 35 is mounted to permit a gross positional adjustment of the wiper blades 49 mounted thereon relative to the corresponding plate 20 against which the wiper blades 49 are engaged.

Each adjustable arm 40 is individually bolted to the block 35 and has three adjustment features to provide flexibility in the loading and positioning of the wiper blades 49 mounted thereon with respect to the corresponding plate 20. Each arm 40 is formed like an automotive wiper arm with an arm head 41 that is bolted to the block 35 and a pivoted arm 42 that is spring-loaded into the extended position seen in FIG. 5 by the spring 43 housed within the arm 42.

The first adjustment feature of the adjustable arm 40 is a spring force adjustment mechanism 45 mounted at the distal end of the arm 40 and connected to the spring 43. The spring force adjustment feature includes a threaded cylinder 46 that is connected to the end of the spring 43 and is threaded onto a screw 47 that is supported by a nut 48 mounted on the arm 40. By rotating the screw 47, the cylinder 46 is moved along the length of the screw 47 to extend or relax the spring 43 by changing the length thereof. In this manner, the force exerted by the spring 43 to urge the wiper blade 49 against the corresponding plate 20 can be varied.

Figure 5:
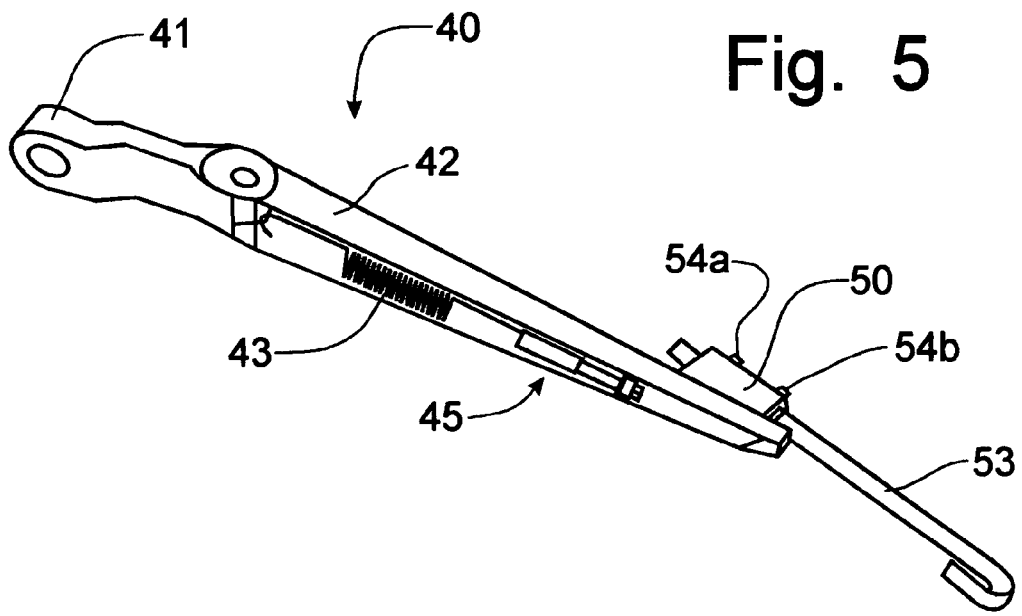
FIG. 5 is a perspective view of a mounting device for a wiper blade located at the head portion of the fixture.
Figure 6:
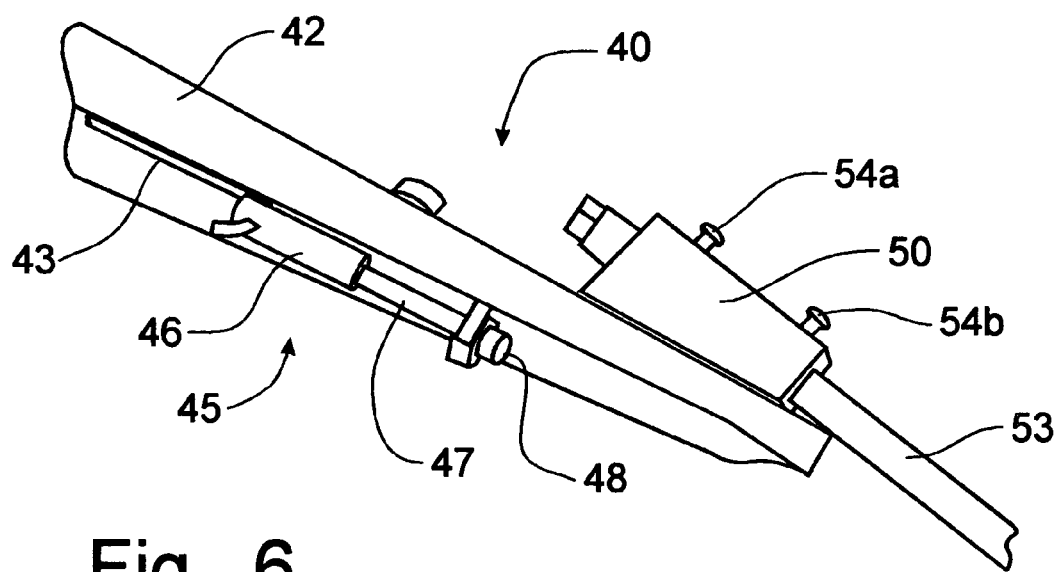
FIG. 6 is an enlarged perspective view of the adjustment apparatus of the mounting device to affect a variation in the load vector and of the attack angle of the wiper blade being tested against the test surface.

The second adjustment feature of the arm 40 is depicted in FIGS. 5-7. A mounting block 50 is affixed to the distal end of the mounting arm 40 and is formed with a bore 52 extending therethrough generally at an angle with the mounting arm 40. A rod 53 is mounted in a grooved cylinder 55, best seen in FIGS. 6 and 7, which, in turn, is received within the bore 52 through the mounting block 50. First and second screws 54a and 54b are threaded into the mounting block 50 to engage the rod 53 within the grooved cylinder 55 and fix the orientation of the rod 53.

The first screw 54a fixes rod 53 into the grooved cylinder 55 within the mounting block 50, while the second screw 54b (closest to the distal end of the mounting arm 40) controls the orientation of the rod 53 within the cylinder 55. The attack angle of the wiper blade 49 relative to the plate 20 can be adjusted by loosening the screws 54a, 54b and rotating the rod 53 within the cylinder 55 to position the wiper portion 49a of the wiper blade 49 relative to the plate 20 to an aged angle, such as is depicted in FIG. 8B, whereupon the screw 54b is then tightened to fix the rod 53 in the desired orientation.

The third adjustment feature of the mounting arm 40 provides the ability to change the rod 53 for an alternative form of the rod 53a, such as is depicted in FIG. 7. To replace the rod 53, the screws 54a, 54b are loosened to permit the rod 53 to slide off the grooved cylinder 55, whereupon the alternate rod 53a is inserted into the grooved cylinder 55 and the first screw 54a is tightened first to fix the rod 53a in the cylinder 55 and then the rod 53a is rotated to the desired aging orientation whereupon the second screw 54b is tightened to fix the alternate rod 53a within the mounting block 50. The alternative rod 53a could be a rod that has a specific attachment for the aging of the wiper blade.

With the wiper blade 49 mounted on the end of the rod 53 and positionally adjusted to the desired orientation of the rod 53 relative to the plate 20, the loading direction can be varied by adjusting the position of the block 35 on the end beam 13 and by adjusting the spring force exerted on the mounting arm 40 through use of the threaded cylinder 46 mounted on the screw 47.

The plates 20 can be adjusted for curvature by manipulating the vertical positions of the bronze nuts 27 on the threaded rods 26. Two plates 20 are preferably provided on each fixture frame 11 so that the curvature of the windshield at the passenger side and at the driver's side can be properly adjusted to conform to the driver's side wiper blade, as opposed to the passenger side wiper blade which is usually shorter than the driver's side blade. Multiple wiper blades can be tested on each plate 20 simultaneously.

The plates 20 have limitations as to adjustment of the curvature to simulate the windshield glass. The smallest radius at which the plates 20 can be curved without subjecting the plates to permanent deformation is 700 mm. If curvature greater than a 700 mm radius is required, two thinner plates 20 are placed on top of one another to provide adequate flexibility while providing support for the wiper blades. Deformation of the plate with loading from the wiper blades should be less than 0.1 mm. To maintain this tolerance, an appropriate number of threaded rods 26 with bronze nuts 27 supporting the adjustable cross bars 30 and securing the plates 20 will need to be utilized.

Accordingly, the flexible fixture 10 described above is capable of replicating the real world environment for the operation of wiper blades for all ranges of production variability in a quick and efficient manner. The fixture 10 is flexible to a large range of wiper blade sizes and is flexible to create a large range of glass curvatures. The fixture 10 is intended to replicate the conditions of the wiper blade when in the park position with the same load bearing and environmental to which the blades are exposed in actual use.

The fixtures 10 can be stacked on top of one another, as is depicted in FIG. 9, to provide the ability to age a large group of wiper blades 49 at the same time and under the same laboratory conditions. By stacking the fixtures 10, the entire group of wiper blades 49 can be inserted into a small volume oven for aging purposes.

The advantages of this fixture 10 are that the equivalent degradation of field returned wiper blades can be replicated on new wiper blades 49. The fixture 10 will age and test different designs of wiper blades 49 and rubber material to permit the most robust design to be selected for production. The fixture 10 is also capable of identifying the effect of blade to blade variability using established wipe quality metrics. Furthermore, the flexibility of the fixtures 10 allows the aging and testing of wiper blades across an entire spectrum of vehicles.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

Having thus described the invention, what is claimed is:

1. A test fixture for aging automotive wiper blades in a laboratory, comprising:
   a frame including side beams and end beams;
   at least one flexible plate being formable into a curved configuration replicating an automotive windshield;
   support members mounted on said side beams to engage said at least one flexible plate to form said at least one flexible plate into said curved configuration; and
   at least one mounting arm supported on said frame at one of said end beams and projecting over said at least one flexible plate, said at least one mounting arm being detachably connectable to a wiper blade for placement thereof in engagement with said flexible plate.

2. The test fixture of claim 1 wherein said frame further includes a center support beam extending between said end beams generally parallel to said side beams, said at least one flexible plate including a first flexible plate supported between one of said side beams and said center support beam, and a second flexible plate supported between the other of said side beams and said center support beam, said support members being mounted on both said side beams and said center support beam.

3. The test fixture of claim 2 wherein said support members are positionally adjustable to support the corresponding said flexible plate at respective heights above said side beams and said center beam to form said curved configuration in said flexible plates.

4. The test fixture of claim 3 wherein said one end beam on which said mounting arms are supported has mounted thereon an elongated support block mounted to said one end beam, said support block has each of said mounting arms affixed thereto, said mounting block being vertically positionable relative to said one end beam to provide vertical positional adjustment to all of said mounting arms simultaneously.

5. The test fixture of claim 3 further comprising a push down bar attached to said frame proximate to each said end beam to restrain a corresponding end of the corresponding said flexible plate to affect said curved configuration.

6. The test fixture of claim 3 wherein each said mounting arm includes a mounting block supported on said mounting arm to receive said a rod on which is mounted a wiper blade for testing, the mounting block further includes a pair of screws engaged into said mounting block to adjust an attack angle of said rod and said wiper blade relative to said mounting arm and relative to the corresponding said flexible plate.

7. The test fixture of claim 6 wherein each said mounting arm includes an adjustable spring supported within said mounting arm to vary selectively a spring-force pressure exerted by said wiper blade against the corresponding said flexible plate.

8. The test fixture of claim 3 wherein said first and second flexible plates can be formed in different curved configurations.

9. The test fixture of claim 8 wherein said support members are arranged in pairs positioned in opposing locations along the corresponding said flexible plate, each said pair of support members supporting an adjustable cross bar oriented generally parallel to said end beams and supporting the corresponding said flexible plate.

10. The test fixture of claim 9 wherein each said support member includes an elongated threaded rod having a pair of nuts threaded thereon, said adjustable cross bar being supported between said nuts and positionable at a selected height above said frame by the positioning of said nuts on said threaded rod.

11. A test fixture for testing vehicle wiper blades in a laboratory, comprising:
    a frame including a pair of longitudinally extending side beams, a pair of transversely oriented end beams, and a center support beam extending between said end beams generally parallel to said side beams;
    first and second flexible plates being formable into respective curved configurations replicating automotive windshields;
    support members mounted on said side beams and said center support beam to engage said flexible plates to form said flexible plates into said curved configurations; and
    a plurality of mounting arms supported on said frame at one of said end beams and projecting over said flexible plates, said mounting arms being detachably connectable to a wiper blade for placement thereof in engagement with said flexible plates.

12. The test fixture of claim 11 wherein said first flexible plate is supported between one of said side beams and said center support beam, and said second flexible plate being supported between the other of said side beams and said center support beam, said support members being mounted on both said side beams and said center support beam to position said flexible members as needed.

13. The test fixture of claim 12 wherein said side beams and said center support beam are formed with apertures into which said support members are engaged.

14. The test fixture of claim 13 wherein said support members are arranged in pairs positioned in opposing locations along the corresponding said flexible plate, each said pair of support members supporting an adjustable cross bar oriented generally parallel to said end beams and supporting the corresponding said flexible plate, each said support member being positionally adjustable to support the corresponding said flexible plate at respective heights above said side beams and said center beam to form said curved configuration in said flexible plates.

15. The test fixture of claim 14 wherein said first and second flexible plates can be formed in different curved configurations.

16. The test fixture of claim 15 wherein each said support member includes an elongated threaded rod having a pair of nuts threaded thereon, said adjustable cross bar being supported between said nuts and positionable at a selected height above said frame by the positioning of said nuts on said threaded rod.

17. The test fixture of claim 16 wherein each said mounting arm includes a mounting block supported on said mounting arm to receive said a rod on which is mounted a wiper blade for testing, the mounting block further including a pair of screws engaged into said mounting block to adjust an attack angle of said rod and said wiper blade relative to said mounting arm and relative to the corresponding said flexible plate, each said mounting arm further including an adjustable spring supported within said mounting arm to vary selectively a spring-force pressure exerted by said wiper blade against the corresponding said flexible plate.

18. A test fixture for conducting laboratory testing of automotive wiper blades comprising:
    a frame including a pair of longitudinally extending side beams, a pair of transversely oriented end beams, and a center support beam extending between said end beams generally parallel to said side beams, each of said side beams and said center support beam having formed therein spaced apart apertures;
    support members mounted in selected said apertures on said side beams and said center support beam, said support members being arranged in opposing pairs with one of said opposing pair of support members being positioned on said center support beam;
    a first flexible plate mounted on said support members between said center support beam and one of said side beams, said first flexible plate being oriented in a curved configuration replicating an automotive windshield;
    a second flexible plate mounted on said support members between said center support beam and the other of said side beams, said second flexible plate also being oriented in a curved configuration; and a plurality of mounting arms supported on said frame at one of said end beams and projecting over said flexible plates, said mounting arms being detachably connectable to a wiper blade for placement thereof in engagement with said flexible plates.

19. The test fixture of claim 18 wherein said each said opposing pair of support members support an adjustable cross bar oriented generally parallel to said end beams and supporting the corresponding said flexible plate, each said support member including an elongated threaded rod having a pair of nuts threaded thereon, said adjustable cross bar being supported between said nuts and positionable at a selected height above said frame by the adjustable positioning of said nuts on said threaded rod, said adjustable cross bar supporting the corresponding said flexible plate at respective heights above said side beams and said center beam to form said curved configuration in said flexible plates.

20. The test fixture of claim 19 wherein each said mounting arm includes a mounting block supported on said mounting arm to receive said a rod on which is mounted a wiper blade for testing, the mounting block further including a pair of screws engaged into said mounting block to adjust an attack angle of said rod and said wiper blade relative to said mounting arm and relative to the corresponding said flexible plate, each said mounting arm further including an adjustable spring supported within said mounting arm to vary selectively a spring-force pressure exerted by said wiper blade against the corresponding said flexible plate.

* * * * *